United States Patent [19]

Briend et al.

[11] Patent Number: 5,670,177

[45] Date of Patent: Sep. 23, 1997

[54] INJECTABLE NO/CO$_2$ GASEOUS MIXTURE

[75] Inventors: Robert Briend, Les Clayes Sous Bois; Marie-Hélène Renaudin, Paris, both of France

[73] Assignee: l'Air Liquide, Societe Anonyme Pour l'Etude et l'Exploitation des Procedes Georges Claude, Paris, France

[21] Appl. No.: 733,919

[22] Filed: Oct. 18, 1996

[30] Foreign Application Priority Data

Oct. 20, 1995 [FR] France ................... 95 12345

[51] Int. Cl.$^6$ .................................. A61K 33/00
[52] U.S. Cl. ........................................ 424/718
[58] Field of Search ........................ 424/700, 718

[56] References Cited

FOREIGN PATENT DOCUMENTS

WO92/10228  6/1992  WIPO .
WO94/00180  1/1994  WIPO .
WO94/22499  10/1994  WIPO .

*Primary Examiner*—Raymond Henley, III
*Attorney, Agent, or Firm*—Burns, Doane, Swecker & Mathis, LLP

[57] ABSTRACT

A method for treating or preventing ischemia comprising administering to a patient by an intravascular route a gaseous mixture comprising nitric oxide (NO) and carbon dioxide (CO$_2$), wherein the nitric oxide is present in an amount effective to treat or prevent ischemia.

A gaseous mixture for treatment or prevention of ischemia comprising:

(i) nitric oxide in an amount effective to prevent ischemia; and
(ii) carbon dioxide.

12 Claims, 1 Drawing Sheet

INJECTABLE NO/CO₂ GASEOUS MIXTURE

BACKGROUND OF THE INVENTION (i) Field of the Invention

The present invention relates to the a method for prevention or treatment of ischemia and, in particular, of embolism by administering to a patient intravenously a stable gaseous mixture based on nitric oxide (NO) and carbon dioxide ($CO_2$).

Nitric oxide is produced naturally in mammals by an enzyme, called NO-synthase, which is expressed in a constituent manner in endothelial cells, in platelets and in the central and peripheral nervous systems. Another form of calcium-independent NO-synthase can be induced by various stimuli (in particular, by liposaccharides) in numerous cells, such as macrophages, lymphocytes, myocardial cells, endothelial cells, and smooth muscle cells.

Nitric oxide is an important biological messenger in mammals, and this molecule plays a decisive role in the local control of hemodynamics.

It has been possible to prove that NO is released by endothelial cells during variations in blood flow rate. Nitric oxide appears to particularly be a major component of the physiological adaptation of vascular diameter with respect to blood perfusion: in the heart, therefore, reactive hyperemia is reduced considerably. Conversely, a chronic increase in the blood flow rate, produced by an arteriovenous fistula increases dependent relaxations of the endothelium.

The capacity of nitric oxide produced by the vascular wall and in the neighboring tissues is remarkable in terms of precisely regulating the vascular tone by adapting the blood flow. By the same token, it has been assumed that NO released during neuronal activity could regulate the tone of cerebral microcirculation, thus combining cerebral activity and blood flow. We also recall the role played by NO in regulating the proliferation of vascular smooth muscle, which is a decisive factor in vascular compliance.

Nitric oxide furthermore controls post-capillary venular permeability.

Nitric oxide also participates in hormonal regulation mechanisms in the kidney, by inhibiting renin release, and in the heart, by inhibiting atrial natriuretic factor (ANF) release.

Finally, in vivo, platelet activation is permanently controlled by endothelial NO and, to a lesser degree, it is controlled by platelet NO-synthase. During aggregation, platelets release nucleotides (ATP, ADP), serotonin, platelet-activating factor (PAF), thromboxane A2, and vasopressin; they can also initiate the coagulation cascade by releasing thrombin. In response to ATP, ADP, serotonin, PAF and thrombin, endothelial cells release NO and prostacyclin which act synergistically to prevent and counter the platelet aggregation process.

The abnormal decline in the nitric oxide rate, observed in numerous pathological conditions, seems to confirm the importance of the role played by it in the body. Such a decline is seen in hypertension, hypercholesterolemia, atherosclerosis and diabetes.

A very early reduction of the basal release of NO would also be responsible for disorders connected to the reperfusion of areas affected by ischemia, such as in coronary thrombosis and vasospasm.

(ii) Description of Related Art

Various vasodilator agents have so far been perfected based on these various findings: these substances, known as nitrovasodilators, produce NO in vivo, thus compensating for a deficiency of endogenous NO. As an example, one might mention molsidomine or sodium nitroprussate, which prevent platelet adhesion and aggregation.

To make up for insufficient NO production, it has also been proposed that L-arginine or its analogs be administered, since L-arginine participates directly in the biosynthesis of nitric oxide, acting as a substrate for NO-synthase.

In view of the significant contribution made by nitric oxide in maintaining low pressure in pulmonary circulation and the importance of the local vasodilator effect resulting from it, it was then suggested that NO be administered by inhalation during treatment of acute pulmonary arterial hypertension. The extensive research done on that point demonstrated the therapeutic efficacy of a gaseous mixture of NO and inhaled nitrogen at doses of between 1 and 20 ppm NO in patients suffering from acute respiratory disorders; a reduction in pulmonary arterial hypertension, possibly accompanied by an improvement in the ventilatory-perfusion ratios by way of a drop in the intrapulmonary shunt have, in effect, been observed.

Nevertheless, administering by inhalation entails the major inconvenience of bringing about the formation of $NO_2$ due to the reaction of the inhaled NO with the oxygen present in the pulmonary alveoli. Nitrogen dioxide is highly toxic to the lungs. Another disadvantage of this method is tied to the need for making the mixture, consisting of nitric oxide, nitrogen and oxygen, in an extemporaneous fashion, so that the time of contact between NO and $O_2$ must be as short as possible.

Moreover, inhalation, according to all evidence, restricts the action of nitric oxide that is exogenous to the ventilated area of the lungs.

An intravascular injection of the mixture used, consisting of nitrogen and NO, as a matter of fact, cannot be considered since it would cause a gaseous embolism.

SUMMARY AND OBJECTS OF THE INVENTION

In view of the foregoing limitations and shortcomings of the prior art approaches to the administration of NO to a patient in need thereof, as well as other disadvantages not specificaly mentioned above, it should be apparent that there still exists a need in the art for effective treatment for prevention of ischemia using NO which does not give rise to an undesirable formation of $NO_2$ and which is convenient to administer. It is, therefore, a primary objective of the present invention to fulfill that need by providing a method for treating or preventing ischemia comprising administering to a patient by an intravascular route a gaseous mixture comprising nitric oxide (NO) and carbon dioxide ($CO_2$), wherein the nitric oxide is present in an amount effective to treat or prevent ischemia In a second aspect, the invention relates to a gaseous mixture for treatment or prevention of ischemia comprising:

(i) nitric oxide in an amount effective to prevent ischemia; and (ii) carbon dioxide.

With the foregoing and other objects, advantages, and features of the invention that will become hereinafter apparent, the nature of the invention may be more clearly understood by reference to the following detailed description of the invention, the appended claims and to the attached figures.

DETAILED DESCRIPTION OF PREFERRED EMBODIMENTS

Figure 1:
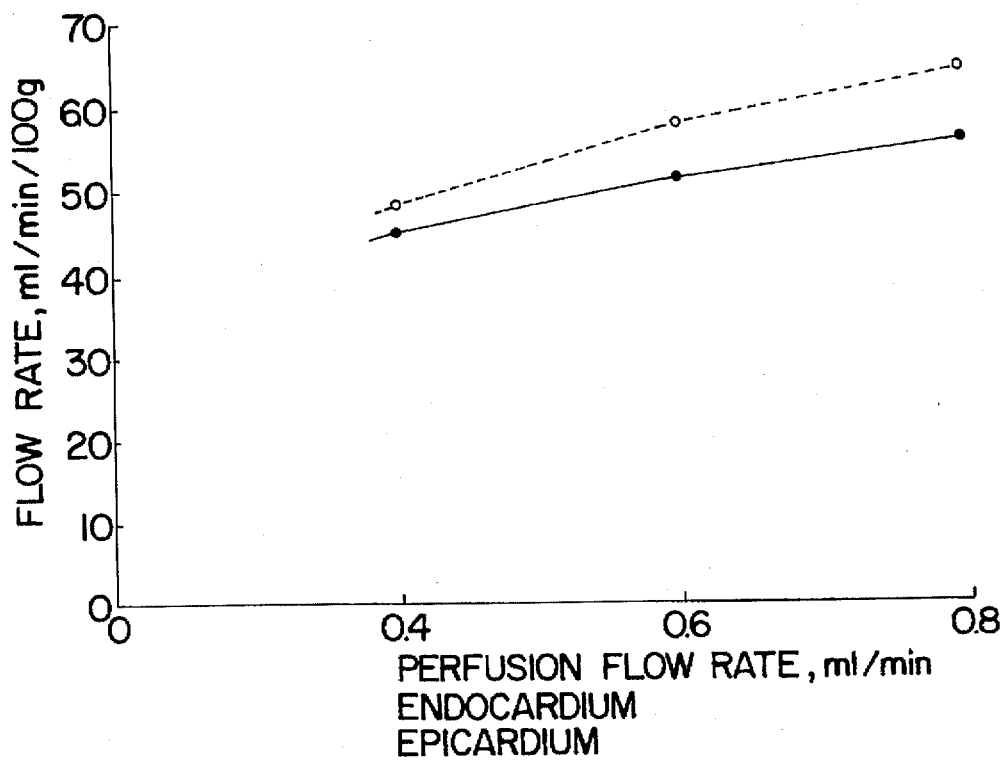
FIG. 1 shows variations in the blood flow rates in the endocardium and epicardium as a function of the perfusion flow rate in healthy rats.

In the context of this invention:

the term ischemia refers to total or partial stoppage of blood circulation in an area located in the human or animal;

and the term embolism indicates an obliteration of a blood vessel by a clot or a foreign body moved by the blood up to the place where the clearance of the blood vessel is insufficient to permit its passage.

An embolism is therefore a particular form of ischemia.

The gaseous medication of the invention preferably comprises a single mixture of carbon dioxide and nitric oxide; however, the addition of at least one gas comprising xenon, krypton, nitrogen protoxide or their mixtures, to the mixture of $CO_2$ and NO is also conceivable in the context of the invention.

The concentration of NO in the gaseous mixture of $NO+CO_2$ is an effective concentration, preferably between 1 and 100 ppm. A concentration of less than 1 ppm is not desirable since a minimum concentration of 2 nM of NO is found in the blood plasma of a healthy mammal. A concentration of more than 100 ppm leads to a progressive disappearance of the therapeutic effect. The reasons for the low activity level observed at such concentrations are still unknown, but could be tied to a local toxicity or possibly saturation of the nitric oxide receptors.

According to a preferred embodiment, the concentration of NO in the medication mixture is between 15 and 30 ppm.

The stability of the gaseous medication involved in the invention makes it possible to store it under pressure in conventional packaging such as steel or light aluminum-based alloy bottles.

Selection of light aluminum-based alloy bottles will prevent any risk of contamination. The preferred storage conditions, which will ensure the stability for more than 2 years, include a temperature between 15° and 30° C., preferably between 20° and 25° C., and a pressure between 20 and 30 bar.

The gaseous medication of the invention can be administered intravascularly, without risk of any gaseous embolism, for example, by intra-arterial administration, by intracardial administration, or by intravenous administration.

In the case of intravascular administration, it is preferable to resort to introducing a catheter into the blood vessel that is to be treated. Catheters that can be used for this purpose are those that are commonly used in the technique. The nature of the material constituting the catheter is not critical in itself; nevertheless, a flexible material such as silastene is preferred. It is implanted in the blood vessel as is commonly done, for example, after local anesthesia and incision. For greater convenience, the catheter can be held in place by a suture, after which the incision may or may not be closed up.

During injection, the usual precautions must be taken to prevent platelet aggregation and coagulation at the injection site.

Along these lines, one could also administer a heparin-treated physiological solution before and after injection of the gaseous medication involved in the invention.

The injection flow rate can be easily determined by a person skilled in the art since immediate solubilization of the gaseous medication, in the course of its administration, is most desirable. In doing so, the formation of gas bubbles will be prevented. In humans, a flow rate of less than 20 ml/min, preferably less than 10 ml/min, better still 8 ml/min, will lead to optimum effectiveness. These figures, however, do not in any way restrict the invention. It is clear, in fact, that the injection rate is a function of the blood flow rate of the treated vessel.

The quantity of the compound to be administered in turn depends on the age of the patient, the seriousness of the disorder from which he suffers, and the concentration of NO in the injected gaseous compound.

According to the invention, administration into an artery is preferred. It was possible to determine that, in the arteries, the concentration in terms of oxyhemoglobin is such that binding of nitric oxide to hemoglobin is definitely disadvantageous. As a result, formation of methemoglobin, due to the binding of NO to hemoglobin, would take place only in a quantity that would be insufficient to cause a possible inhibition of the therapeutic effect of nitric oxide and, in particular, its vasodilator and platelet anti-aggregation action.

Recent work has shown that nitric oxide can also react with proteins, such as albumin, to form S-nitrosothiols whose half-life is longer than that of free NO. These species represent a biological activity that is comparable to that of free NO; we therefore understand that the effectiveness of the compounds involved in the invention is not diminished.

The medicinal compounds involved in the invention are perfectly suitable for the treatment of ischemia and embolism when administered by intravascular, intra-arterial, intra-cardial, or intravenous injection.

Examples 1 through 3 below illustrate the stability of the compounds involved in the invention, as well as their therapeutic usefulness, with reference to FIGS. 1 and 2, attached. These examples are merely presented by way of illustration and should in no way be construed as limiting the subject matter disclosed and claimed.

EXAMPLE 1

Various mixtures of nitric oxide and carbon dioxide were prepared and packaged in type B5 bottles made of a light aluminum-based alloy, sold by S.M. GERZAT, under a pressure of 24 bars. The initial concentration of the nitric oxide was set at 20 ppm in these mixtures. The stability of the NO concentration was studied for three bottles kept at ambient temperature over a period of 16 months.

The NO concentration is measured by a chemiluminescence analyzer in the range of 0 to 100 ppm, calibrated before each measurement using a standard $NO/N_2$ mixture at 90 ppm. The chemiluminescence analyzer used is the TOPAZE 2020 made by COSMA.

At the end of a period of 16 months, it was impossible to detect any decomposition of the nitric oxide in the $NO/CO_2$ mixtures that were kept at ambient temperature. Actually, the only fluctuations that were measured in the value of NO concentration remained less than analytically precise.

These results confirmed the stability of the medicinal compounds involved in the invention.

EXAMPLE 2

The therapeutic usefulness of the medicinal compounds of the invention was demonstrated with the help of an experimental model. More precisely, this example is intended to provide evidence of in vivo vasodilator properties of gaseous compounds made up of a mixture of $CO_2$ and NO in the heart, using a model of multifocal myocardial ischemia in rats.

This test was performed on male Wistar rats with an average weight of 260/280 g, aged 3 months.

For the administration of the compounds involved in the invention, we inserted indwelling catheters that emptied out into the left ventricle.

The rats were fasted for 20 hours prior to experimentation.

Chloral hydrate anesthesia was administered intraperitoneally at a dose of 360 mg/kg. The left carotid was separated and clamped without damaging the muscle. A flexible silastene catheter, filled with 2% heparin-treated physiological solution was introduced by retrograde administration up to the left ventricle (about 5 cm of catheter). The catheter was held in place by two sutures and exited by passing under the skin of the dorsal portion of the head. The incision was closed up again. The animal was aroused from anesthesia within 60 to 90 minutes. The permeability of the catheter was checked, as was the heparin-treated physiological solution that remained in the catheter.

Just three hours after awaking, the spontaneous activities of the animals returned to normal. The end of the catheter was extended with a conventional catheter (Biotrol) with an inside diameter of 600 µ and a length of 30 cm for further injections.

Various experiments were performed on a group of healthy rats and on a group of embolized rats.

Here is the surgical record that was tracked to induce multifocal myocardial ischemia.

Embolization was caused by administration, in a healthy rat, of 0.4 ml of 20% dextran, containing 40,000 microspheres of 50 µ albumin, microtested and kept in suspension by stirring. The injection is conducted over 1 minute by means of an interventricular catheter.

0.2 ml of physiological solution are then administered by the same way to push the assembly of microspheres into the ventricle. These microspheres are distributed in the body as a function of heart flow rate fractions and, in particular, enter the myocardium. Each microsphere obturates an artery and brings about a microembolization. After the administration of the microspheres, 30 minutes pass during development of ischemia before the appearance of edema. The rats in the other remaining part of the group are not embolized.

The catheter is then connected to a gas flow regulator connected to a source for gas that is to be injected.

Indocyanine green (10 µl) is placed in the catheter to display the movement of the physiological solution. The gas flow rate regulator is opened and the gas is pushed at a constant rate into the catheter for one minute.

After one minute has gone by, the catheter is disconnected from the regulator, and the rest of the gas, located in the catheter, is pushed by 0.2 ml of physiological solution.

Immediately (10 seconds) afterward, a solution of isopropyl iodoamphetamine (IAMP) labeled with (125)iodine, in a 0.2 ml volume, is administered the same way and is pushed by 0.2 ml of physiological solution. The rats are decapitated 5 minutes after this last administration. Blood is drawn with heparin and is rapidly centrifuged to isolate the plasma and the erythrocytes. About 200 mg of liver are sampled. The heart is excised and separated into endocardium and epicardium by dissection.

The radioactivity of the four tissues, plasma, liver, epicardium and endocardium, is then counted by gamma spectrometry (Appareil Intertechnique), setting the A channel to (125)iodine.

The results obtained are expressed in terms of numbers of counts per minute and in grams of tissues.

The radioactivity of the plasma enabled the calculation of a blood flow rate in each tissue, considering the average heart flow rate which is 180 ml/min in rats.

The tissue flow rates are expressed in terms of ml/min/100 g of tissue.

EXAMPLE 2A

A first series of experiments was conducted using the general protocol presented above, starting with 12 rats, 6 healthy ones and 6 embolized ones, without injection of gas.

The corresponding control values for the blood flow rates are given below in Table A:

TABLE A

|  | Blood Flow Rate (ml/min/100 g) | |
| --- | --- | --- |
|  | Control Rats | Embolized Rats |
| Endocardium | 28.7 ± 1.4 | 20.5 ± 1.1** |
| Epicardium | 24.6 ± 1.1 | 23.3 ± 0.8 |
| R = Endo/Epi | 1.16 ± 0.15 | 0.87 ± 0.02** |
| Liver | 73 ± 3 | 68 ± 3 | n = 6, m ± ESM,
**p = 0.01 (the t test of Student) comparison between embolized or nonembolized [rats].

The basal flow rate of the endocardium is greater than that of the epicardium, so that the ratio of endocardium with respect to epicardium is greater than 1. Embolization involves the endocardium much more than the epicardium, hence there is a significant inversion of the ratio. Embolization causes a significant decline in the heart flow rates, whereas in the liver, the reference organ, the decrease observed is very small.

EXAMPLE 2B

A second series of experiments was performed along the lines of the general protocol given in Example 2, using a group of six healthy rats to whom mixtures of NO and $CO_2$ were administered.

NO was perfused for one minute at doses of 20 ppm with a flow rate of 0.4, 0.6 and 0.8 ml/min, and 200 ppm with a flow rate of 0.6 ml/min.

Table B below shows all of the results that were obtained.

TABLE B

| | Blood Flow Rate (ml/min/100 g) | | | |
|---|---|---|---|---|
| | C1 = 20 ppm<br>d2 = 0.4 ml/min | C1 = 20 ppm<br>d2 = 0.6 ml/min | C1 = 20 ppm<br>d2 = 0.8 ml/min | C1 = 200 ppm<br>d2 = 0.6 ml/min |
| Endocardium | 44.8 ± 1.0 | 51.2 ± 1.2 | 55.8 ± 1.4 | 34.5 ± 1.4 |
| Epicardium | 48.2 ± 1.5 | 57.8 ± 1.7 | 64.2 ± 1.2 | 36.7 ± 1.6 |
| R = Endo/Epi | 0.93 ± 0.02 | 0.89 ± 0.01 | 0.87 ± 0.01 | 0.94 ± 0.01 |
| Liver | 79 ± 4 | 78 ± 4 | 74 ± 2 | 66 ± 6 | n = 6, m ± ESM.
1: C shows the concentration of NO in the administered gas.
2: d represents the gas flow rate during injection.

The flow rates at the level of the endocardium and the epicardium are increased significantly by small doses of NO.

FIG. 1, attached, plotted on the basis of the results obtained from examples 2A and 2B, shows variations in the blood flow rates in the endocardium and epicardium as a function of the perfusion flow rate in healthy rats. This curve clearly shows that the tissue blood flow rate increases in proportion to the perfusion flow rate, that is, to the total quantity of injected NO.

Nevertheless, there is a definite decline in the blood flow rates with a major increase (by a factor of 10) of the NO concentration in the administered gas.

EXAMPLE 2C

A third series of experiments was carried out using the general protocol given in Example 2, using a group of six embolized rats to whom mixtures of NO and $CO_2$ were administered.

The NO was perfused for one minute at doses of 20 ppm with a flow rate of 0.4, 0.6 and 0.8 ml/min, and 200 ppm with a flow rate of 0.6 ml/min.

TABLE C

| | Blood Flow Rate (ml/min/100 g) | | | |
|---|---|---|---|---|
| | C1 = 20 ppm<br>d2 = 0.4 ml/min | C1 = 20 ppm<br>d2 = 0.6 ml/min | C1 = 20 ppm<br>d2 = 0.8 ml/min | C1 = 200 ppm<br>d2 = 0.6 ml/min |
| Endocardium | 42.2 ± 1.3 | 46.2 ± 1.5 | 51.8 ± 1.5 | 38.0 ± 1.8 |
| Epicardium | 41.2 ± 1.4 | 43.2 ± 1.0 | 44.2 ± 1.3 | 38.8 ± 2.0 |
| R = Endo/Epi | 1.03 ± 0.03 | 1.07 ± 0.02 | 1.17 ± 0.03 | 0.98 ± 0.01 |
| Liver | 69 ± 3 | 68 ± 3 | 67 ± 3 | 68 ± 3 | n = 6, m ± ESM.
1: C shows the concentration of NO in the administered gas.
2: d represents the gas flow rate during injection.

By virtue of the administered dose, NO brings about an increase in the flow rate in the endocardium. To a lesser extent, one can observe an identical effect on the level of the epicardium. This is expressed by a restoration of the R ratio as in the controls.

Figure 2:
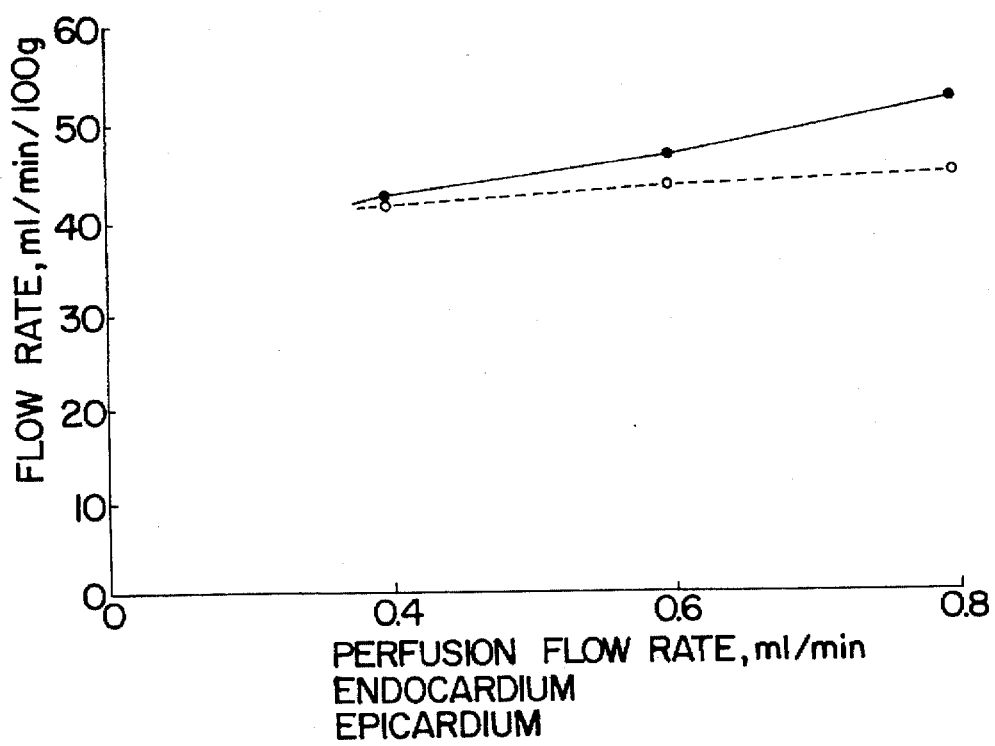
FIG. 2 shows variations of the blood flow rates in the epicardium and endocardium as a function of the flow rate of the injected gas.

FIG. 2 compiles the results obtained in this example and those from Example 2A, involving embolized animals that did not undergo any administration of gas. More precisely, the curve in FIG. 2 traces the variations of the blood flow rates in the epicardium and endocardium as a function of the flow rate of the injected gas.

Compared to the nonembolized animals, NO, in small doses, brings about a redistribution of flow rates toward the endocardium, which is the region that is most heavily subjected to ischemia. This effect is associated with an overall increase in the flow rate.

NO thus redistributes blood toward the most heavily embolized regions, hence the usefulness of the compounds involved in the invention in the treatment of acute infarct.

This experiment definitely evidences the absence of activity of NO administered in the liver, confirming the local action of nitric oxide. We once again find that the therapeutic effect is diminished when the concentration of NO in the injected gas is too high (200 ppm).

After each administration of gas (Examples 2B and 2C), blood was sampled from each rat. The erythrocytes isolated from the plasma were hemolyzed and the percentage of methemoglobin in relation to hemoglobin was determined by ultraviolet spectrometry, using a UNICAM apparatus. It was impossible to detect any change in the methemoglobin rate when compared to a sample of control rat blood.

EXAMPLE 3

This example is a study of the possible toxicity of gaseous NO administered intracardially. Using the same administration record as given in Example 2A, the following three experiments were carried out:

EXAMPLE 3A

Two rats received a perfusion of $NO+CO_2$ at a concentration of 200 ppm of NO and a flow rate of 0.8 ml/min for 15 minutes. Passing behavior disorders were observed during and at the end of perfusion; then the rats recovered normal behavior (no mortality after eight days).

EXAMPLE 3B

Four rats received a perfusion of $NO+CO_2$ at a concentration of 200 ppm and a flow rate of 1.2 ml/min for 15 minutes. After convulsions, the animals developed a paralysis of the hindquarters. Two of the four animals died within an hour after the end of perfusion. The other two survived but remained partly paralyzed.

EXAMPLE 3C

Two rats received a perfusion of $CO_2$ at a flow rate of 1.2 ml/min for 15 minutes. Paralysis of the hindquarters was observed, without mortality.

The perfusion of $NO+CO_2$ at a concentration of 200 ppm and a flow rate of 1.2 ml/min for 15 minutes resulted in 50% mortality of the animals, whereas a flow rate of 0.8 ml/min did not yield any mortality. It seems, however, that the speed of perfusion would be decisive since $CO_2$ turns out to be almost as toxic.

It thus appears that the toxic doses are definitely more important than the active doses; this permits therapeutic use of the compounds involved in the invention without any major risk.

Although only preferred embodiments of the invention are specifically illustrated and described above, it will be appreciated that many modifications and variations of the present invention are possible in light of the above teachings and within the purview of the appended claims without departing from the spirit and intended scope of the invention.

We claim:

1. A gaseous mixture for treatment or prevention of ischemia comprising:
   (i) nitric oxide in an amount effective to prevent ischemia;
   (ii) carbon dioxide; and
   (iii) nitrogen protoxide.

2. The gaseous mixture of claim 1 wherein said gaseous mixture further comprises at least one of xenon, krypton, and their mixtures.

3. The gaseous mixture of claim 1, wherein said gaseous mixture comprises a concentration of NO between 1 and 100 ppm.

4. The gaseous mixture according to claim 1 wherein said gaseous mixture comprises a concentration of NO between 15 and 30 ppm.

5. A method for treating or preventing ischemia comprising administering to a patient by an intravascular route a gaseous mixture comprising nitric oxide (NO) and carbon dioxide ($CO_2$), wherein said nitric oxide is present in an amount effective to treat or prevent ischemia.

6. A method for treating or preventing embolism comprising administering to a patient by an intravascular route a gaseous mixture comprising nitric oxide (NO) and carbon dioxide ($CO_2$), wherein said nitric oxide is present in an amount effective to treat or prevent embolism.

7. The method according to claim 5, wherein said gaseous mixture further comprises at least one of nitrogen protoxide, xenon, krypton, and their mixtures.

8. The method according to claim 5 wherein said gaseous mixture comprises a concentration of NO between 1 and 100 ppm.

9. The method according to claim 5 wherein said gaseous mixture comprises a concentration of NO between 15 and 30 ppm.

10. The method according to claim 5 wherein said intravascular route is an intra-arterial route.

11. The method according to claim 5 wherein said intravascular route is an intracardial route.

12. The method according to claim 5 wherein said intravascular route is an intravenous route.

* * * * *